(12) United States Patent  
Kim et al.

(10) Patent No.: US 9,999,391 B2  
(45) Date of Patent: Jun. 19, 2018

(54) WEARABLE ELECTROMYOGRAM SENSOR SYSTEM

(71) Applicant: KOREA INSTITUTE OF SCIENCE AND TECHNOLOGY, Seoul (KR)

(72) Inventors: Keehoon Kim, Seoul (KR); Sin-Jung Kim, Seoul (KR); Min Kyu Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 205 days.

(21) Appl. No.: 14/088,859

(22) Filed: Nov. 25, 2013

(65) Prior Publication Data

US 2014/0364703 A1 Dec. 11, 2014

(30) Foreign Application Priority Data

Jun. 10, 2013 (KR) .................. 10-2013-0065679

(51) Int. Cl.
*A61B 5/00* (2006.01)
*A61B 5/04* (2006.01)
(Continued)

(52) U.S. Cl.
CPC .......... *A61B 5/6831* (2013.01); *A61B 5/0492* (2013.01); *A61B 5/1123* (2013.01);
(Continued)

(58) Field of Classification Search
CPC ... A61B 5/0492; A61B 5/6831; A61B 5/6824; A61B 5/1123; A61B 5/04017; A61B 5/7455; G06F 3/015
See application file for complete search history.

(56) References Cited

U.S. PATENT DOCUMENTS

2004/0133081 A1* 7/2004 Teller ...................... A61B 5/01  
600/300  
2005/0283204 A1* 12/2005 Buhlmann ........... A61B 5/1107  
607/48

(Continued)

FOREIGN PATENT DOCUMENTS

JP 2011-156376 A 8/2011  
KR 10-2005-0065197 A 6/2005  
(Continued)

OTHER PUBLICATIONS

Yang et al. "Dynamic Hand Motion Recognition Based on Transient and Steady-State EMG Signals," International Journal of Humanoid Robotics vol. 9, No. 1 (2012).*

*Primary Examiner* — Michael C Stout  
(74) *Attorney, Agent, or Firm* — NSIP Law

(57) ABSTRACT

A wearable electromyogram sensor system is provided. The wearable electromyogram sensor system includes: an elastic band having a plurality of electrodes; an electromyogram sensor including an electrode connected to an electrode of the band so as to receive a bio-signal related to contraction of a muscle, and configured to sense a change of motion information through the bio-signal or previously sense the change of the motion information before the motion information is changed; and a fixing unit fixing the electromyogram sensor to the band. The electrode of the electromyogram sensor is connected to an electrode at an arbitrary position of the band.

19 Claims, 7 Drawing Sheets

(51) Int. Cl.
*A61B 5/22* (2006.01)
*A61B 5/0492* (2006.01)
*A61B 5/11* (2006.01)
*G06F 3/01* (2006.01)
*A61B 5/1455* (2006.01)

(52) U.S. Cl.
CPC ............ *A61B 5/6824* (2013.01); *G06F 3/015* (2013.01); *A61B 5/04017* (2013.01); *A61B 5/14551* (2013.01); *A61B 5/7455* (2013.01); *A61B 2562/043* (2013.01)

(56) References Cited

U.S. PATENT DOCUMENTS

| | | | | |
|---|---|---|---|---|
| 2006/0015470 A1* | 1/2006 | Lauer | ............ | A61B 5/0488 706/8 |
| 2008/0009771 A1* | 1/2008 | Perry | ............ | B25J 9/0006 600/587 |
| 2009/0326406 A1* | 12/2009 | Tan | ............ | G06F 1/163 600/546 |
| 2010/0042012 A1* | 2/2010 | Alhussiny | ............ | A61B 5/0428 600/546 |
| 2010/0081913 A1* | 4/2010 | Cross | ............ | A61B 5/04085 600/386 |
| 2010/0198044 A1* | 8/2010 | Gehman | ............ | A61B 5/0408 600/393 |
| 2011/0098593 A1* | 4/2011 | Low | ............ | A61B 5/0006 600/544 |
| 2011/0237972 A1* | 9/2011 | Garfield | ............ | A61B 5/04882 600/546 |
| 2012/0116256 A1* | 5/2012 | Stavdahl | ............ | A61B 5/04888 600/595 |
| 2012/0172682 A1* | 7/2012 | Linderman | ............ | A61B 5/0476 600/301 |
| 2012/0188158 A1* | 7/2012 | Tan | ............ | A61B 5/0488 345/156 |
| 2012/0203725 A1* | 8/2012 | Stoica | ............ | G06F 3/015 706/46 |
| 2012/0245439 A1* | 9/2012 | Andre | ............ | A61B 5/0205 600/310 |
| 2012/0330179 A1* | 12/2012 | Yuk | ............ | A61B 5/0408 600/547 |
| 2013/0123568 A1* | 5/2013 | Hamilton | ............ | A61N 1/36003 600/13 |
| 2013/0190658 A1* | 7/2013 | Flaction | ............ | A61B 5/1038 600/595 |
| 2013/0317648 A1* | 11/2013 | Assad | ............ | B25J 9/1694 700/258 |
| 2013/0338540 A1* | 12/2013 | Hargrove | ............ | A61B 5/11 600/595 |
| 2014/0200432 A1* | 7/2014 | Banerji | ............ | A61B 5/0488 600/383 |
| 2015/0045693 A1* | 2/2015 | Otsamo | ............ | A61B 5/1104 600/554 |
| 2015/0072326 A1* | 3/2015 | Mauri | ............ | A61B 5/0488 434/247 |

FOREIGN PATENT DOCUMENTS

| | | |
|---|---|---|
| KR | 10-2010-0078089 A | 7/2010 |
| KR | 10-2012-0094857 A | 8/2012 |
| KR | 10-2013-0034896 A | 4/2013 |
| WO | WO 2005/048824 A2 | 6/2005 |

* cited by examiner

WEARABLE ELECTROMYOGRAM SENSOR SYSTEM

CROSS-REFERENCE TO RELATED APPLICATION

This application claims priority to Korean Patent Application No. 10-2013-0065679, filed on Jun. 10, 2013, and all the benefits accruing therefrom under 35 U.S.C. § 119, the contents of which in its entirety are herein incorporated by reference.

BACKGROUND

1. Field

Exemplary embodiments relate to a wearable electromyogram sensor system, and more particularly, to a wearable electromyogram sensor system which may be applied to users having a variety of physical features through an elastic band and an electromyogram sensor, and may predict a motion from bio-signals measured through the electromyogram sensor before a user executes a motion, thereby performing a motion intended by the user.

2. Description of Related Art

An electromyogram sensor serves to sense current changes which occur due to movement of muscles, and a variety of researches have been recently conducted on the electromyogram sensor.

In connection with the electromyogram sensor, Korean Patent Publication No. 2005-0065197 has disclosed an interface device which is worn on a user's arm and hand to issue an input/output command related to software contents. The interface device includes a unit to process an input value, obtained from a sensor for tracing motions of the arm and hand, into a predetermined command, and a unit to output an output value of the software contents as predetermined visual, hearing, and tactile stimuli. The interface device proposes an interface design considering wearability for active body parts. Furthermore, Korean Patent Publication No. 2010-0078089 has disclosed a wireless electromyogram measurement system which includes a wireless transmitter module provided for an electromyogram sensing module and a wireless receiver module provided for an electromyogram terminal. Since the electromyogram sensing module may wirelessly transmit an electromyogram signal to the electromyogram terminal, a cable may be prevented from being damaged through frequent use, and inconvenience felt by a subject may be minimized.

The conventional systems have proposed specific applications of the electromyogram sensor, but have not proposed a method for easily applying an electromyogram sensor to users having various physical features.

Furthermore, much research has not been conducted on a method capable of predicting an intended motion of a user based on a measurement signal sensed by the electromyogram sensor and utilizing the predicted motion.

Furthermore, errors caused by the posture, movement, and fatigue of a wearer, which may occur when the electromyogram sensor is substantially applied, may not be reflected. In this case, the wearer's motion cannot be recognized with precision.

SUMMARY

An embodiment of the present invention is directed to a wearable electromyogram sensor system which not only may apply an electromyogram sensor to users having various physical features through an elastic band and an electromyogram sensor, but also may easily apply an electromyogram sensor to user's body parts having different thicknesses, such as wrist and ankle, without a separate control unit.

Another embodiment of the present invention is directed to a wearable electromyogram sensor system which may recognize a motion of a body part after the motion was executed or predict a motion from bio-signals measured from an electromyogram sensor before the motion is executed, thereby executing a motion intended by a user.

Another embodiment of the present invention is directed to a wearable electromyogram sensor system which may reflect a movement and posture so as to more precisely recognize a motion.

Another embodiment of the present invention is directed to a wearable electromyogram sensor system which may reduce an error occurring due to fatigue of a wearer, thereby improving reliability.

In accordance with an embodiment of the present invention, a wearable electromyogram sensor system includes: an elastic band having a plurality of electrodes installed through a surface thereof; an electromyogram sensor including an electrode connected to an electrode of the band so as to receive a bio-signal related to contraction of a muscle, and configured to sense a change of motion information including one or more of a user's motion, a direction of force, a magnitude of force, and energy distribution through the bio-signal or previously sense the change of the motion information before the motion information is changed; and a fixing unit fixing the electromyogram sensor to the band. The electrode of the electromyogram sensor is connected to an electrode at an arbitrary position of the band.

The fixing unit may include one of a magnet, Velcro, and a detachable tape, which are attached to the band and the electromyogram sensor.

The electromyogram sensor may include: an amplification and filtering module configured to amplify and filter the bio-signal; a movement measurement sensor configured to measure a movement and posture of a part to be measured in a state where the electromyogram sensor is coupled to the band; a muscle fatigue measurement module configured to mechanically or optically measure fatigue accumulated in the muscle; and an electrode contact sensing module configured to sense a contact state between the electrode of the band and the electrode of the electromyogram sensor.

In accordance with another embodiment of the present invention, there is provided a wearable electromyogram sensor system which is worn on a user so as to sense bio-signals related to contraction of muscles. The wearable electromyogram sensor system includes an electromyogram sensor having an electrode to receive the bio-signals and configured to sense a change of motion information including one or more of a user's motion, a direction of force, a magnitude of force, and energy distribution through the bio-signals or previously sense the change of the motion information before the motion information is changed.

The electromyogram sensor may include: an amplification and filtering module configured to amplify and filter the bio-signals; a movement measurement sensor configured to measure a movement and posture of a part to be measured; and a muscle fatigue measurement module configured to mechanically or optically measure fatigue accumulated in the muscle.

The wearable electromyogram sensor system may further include: a controller configured to analyze a pattern of the bio-signal and sense or previously sense the change of the motion information; and a conversion module configured to convert the motion information into one or more of motion, energy, force, sound, image, tactility, and data based on the pattern analysis for the motion information.

The controller may include: a muscular contraction signal processing module configured to individually or integrally amplify or attenuate the bio-signals transmitted from the electromyogram sensor; a training module configured to previously receive information on a user's movement, posture, and muscle contraction which occur before a predetermined motion of the user; a pattern analysis module configured to analyze a pattern of the user's motion based on the bio-signals measured by the electromyogram sensor and information inputted from the training module; and a signal input storage module configured to receive and store the bio-signals measured by the electromyogram sensor in real time.

The controller may further include a muscular contraction signal control module configured to control amplification and attenuation for the bio-signals, for the pattern analysis of the pattern analysis module.

The controller may further include a command block module configured to determine that a muscular contraction signal is abnormal when muscle fatigue exceeds a predetermined critical value, and block a command based on the user's bio-signals from being transmitted to the conversion module.

The conversion module may include a device to convert sign language into sound based on pattern analysis for a motion of a user wearing the electromyogram sensor.

The conversion module may include an actuator configured to convert the motion information sensed by the electromyogram sensor into the same motion as or motion corresponding to the motion information.

The conversion module may include a remote control device or orthosis to convert the motion information sensed by the electromyogram sensor into the same motion as or motion corresponding to the motion information, while separated from a user.

The electromyogram sensor may include a display module configured to display one or more of a sound signal, an image signal, and a tactile signal corresponding to the sensed motion information.

DETAILED DESCRIPTION

Figure 1:
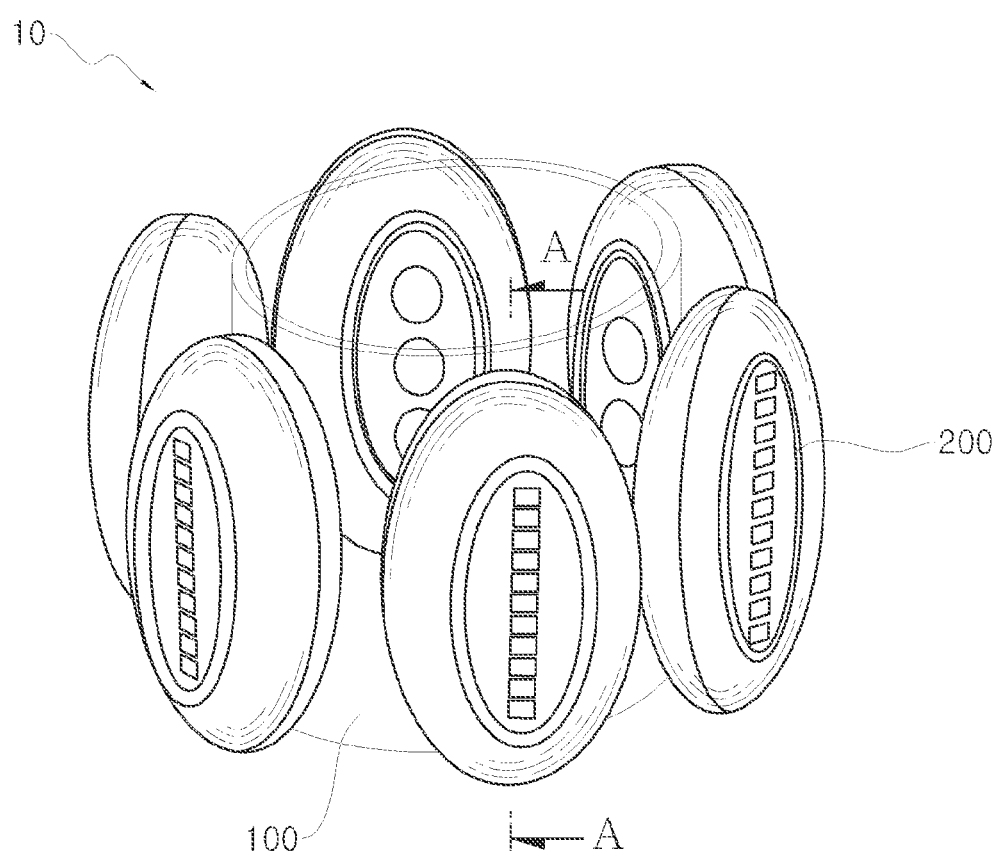
FIG. 1 is a perspective view of a wearable electromyogram sensor system in accordance with an embodiment of the present invention.

Exemplary embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

Figure 2:
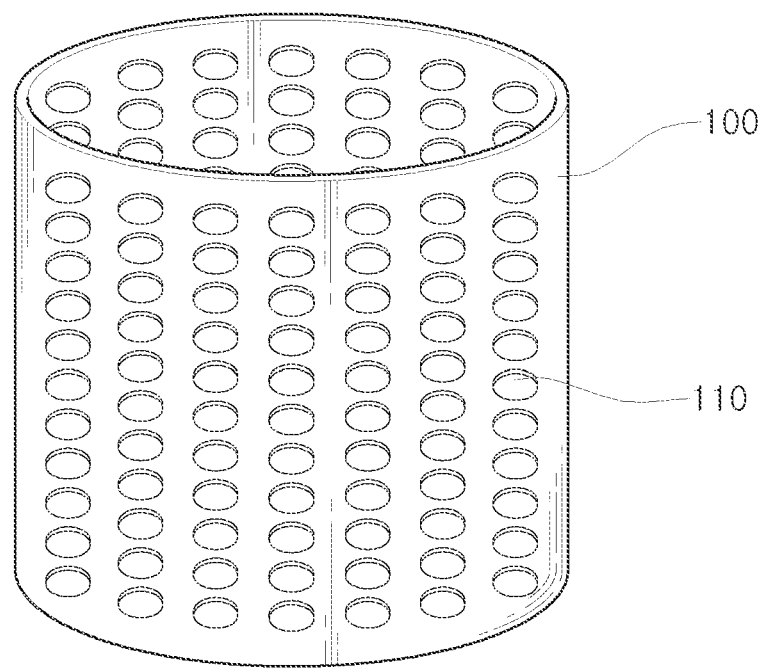
FIG. 2 is a perspective view of an elastic band of FIG. 1.
Figure 3A:
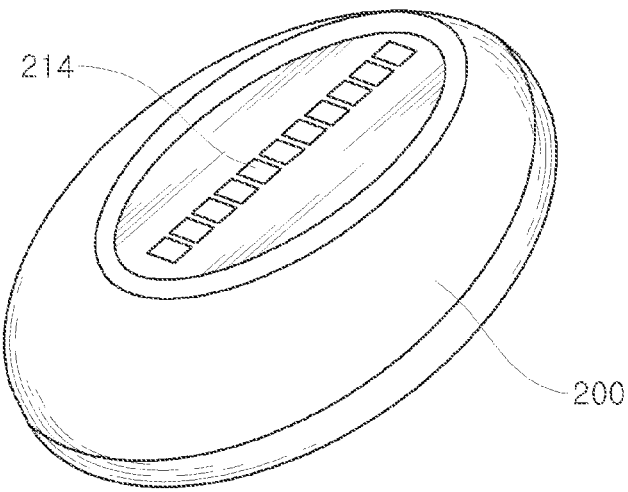
FIG. 3A is a perspective view of an electromyogram sensor of FIG. 1, when seen from the top.
Figure 3B:
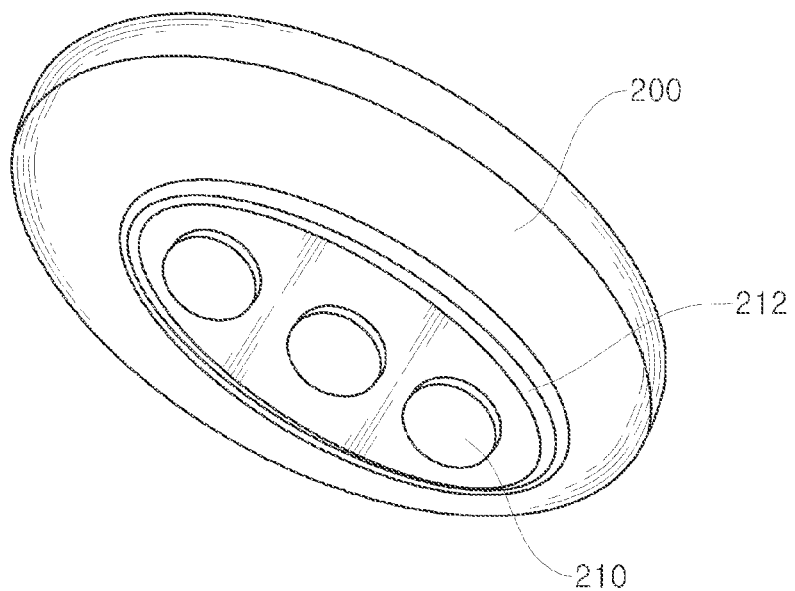
FIG. 3B is a perspective view of the electromyogram sensor, when seen from the bottom.
Figure 4:
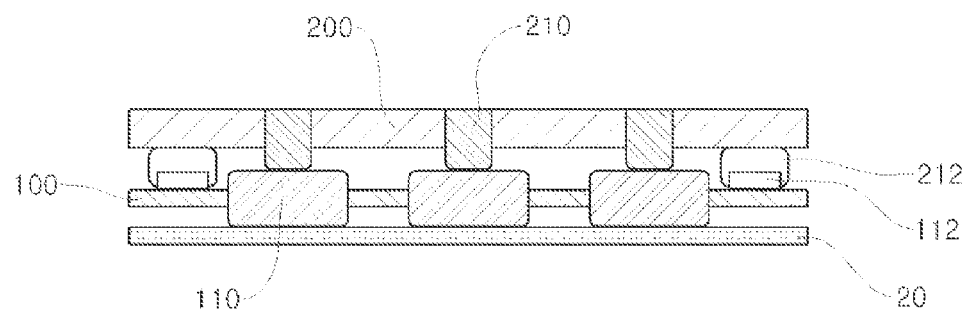
FIG. 4 is a cross-sectional view of the wearable electromyogram sensor system of FIG. 1, taken along line A-A.

FIG. 1 is a perspective view of a wearable electromyogram sensor system in accordance with an embodiment of the present invention. FIG. 2 is a perspective view of an elastic band of FIG. 1. FIGS. 3A and 3B are perspective views of an electromyogram sensor of FIG. 1. FIG. 3A is a perspective view of the electromyogram sensor, when seen from the top, and FIG. 3B is a perspective view of the electromyogram sensor, when seen from the bottom. FIG. 4 is a cross-sectional view of the wearable electromyogram sensor system of FIG. 1, taken along line A-A.

Referring to FIGS. 1 to 4, the wearable electromyogram sensor system 10 according to the embodiment of the present invention includes an electromyogram sensor 200, and the electromyogram sensor 200 may be mounted on a user through a band 100.

In FIG. 2, the band 100 may be expanded and contracted, and includes a plurality of electrodes 110 installed through the surface thereof. Since the band 100 may be expanded and contracted, various users having different physical features may wear the band 100, and one user may easily wear the band 100 on his/her body parts having different thicknesses, such as the wrist and ankle.

The wearable electromyogram sensor system 10 according to the embodiment of the present invention includes the band 100 and the electromyogram sensor 200 which may be separated from each other. Thus, a user may easily wear the band 100 and then couple the electromyogram sensor 200 to a desired position of the band 100, which makes it possible to guarantee the user's activity.

Furthermore, since the band 100 may be expanded and contracted, the band 100 may be closely attached to the user's skin once the user wears the band 100. Thus, electromyogram signals of the user may be reliably transmitted through the electrodes 110 of the band 100.

In accordance with the embodiment of the present invention, the wearable electromyogram sensor system includes an electromyogram sensor 200 which has an electrode 210 to receive electromyogram signals and serves to sense a change of motion information including one or more of a user's motion, a direction of force, a magnitude of force, and energy distribution through the bio-signals or previously sense the change of the motion information before the motion information is changed.

In this specification, 'motion information' is related to a motion intended by a user, and indicates information on one or more of a motion, a magnitude of force, a direction of force, and energy distribution.

In this specification, 'predicting' a motion indicates previously sensing wearer's motion information before the motion information is changed, and 'recognizing' a motion indicates recognizing a change of wearer's motion information after the wearer's motion information started to be changed.

A method for recognizing or predicting motion information using bio-signals such as electromyogram signals will be described below.

In FIG. 1, the electrode 210 of the electromyogram sensor 200 is connected to the electrode 110 of the band 100, and serves to sense a user's bio-signal, that is, an electromyogram signal. For example, a surface electromyogram (SEMG) signal may be sensed.

In order to receive a bio-signal such as an electromyogram signal, the electromyogram sensor 200 may be attached on a user's skin or may be attached on the user's skin through an auxiliary unit.

In FIG. 1, the electromyogram sensor 200 is fixed to the band 100 so as to be attached to a user's skin. As the electrode 210 of the electromyogram sensor 200 and the electrode 110 of the band 100 are connected to each other, conductivity may be guaranteed through a high conductivity solution. FIG. 3B illustrates that the electromyogram sensor 200 includes three electrodes 210. However, the number of electrodes 210 is not limited to three, but the electromyogram sensor 200 may include three or less electrodes or three or more electrodes.

In accordance with the embodiment of the present invention, the wearable electromyogram system 10 may fix the electromyogram sensor 200 to the band 100 through a fixing device. Specifically, the fixing device may include a magnet, Velcro, a detachable tape or the like. The fixing device is not limited thereto, but various fixing units may be applied.

Referring to FIG. 3A, the wearable electromyogram sensor system 10 according to the embodiment of the present invention includes a fixing unit for fixing the electromyogram sensor 200 to the band 100. For this structure, a magnet 212 may be installed around the electrode 210 of the electromyogram sensor 200, and a magnet 112 having a different polarity from the magnet 212 of the electromyogram sensor 200 may be installed on the surface of the band 100 such that the electromyogram sensor 200 is fixed to the band 100 through magnetic force.

Referring to FIG. 3A, the electromyogram sensor 200 may include a display module 214 to display one or more of a sound signal, a image signal, and a tactile signal corresponding to the sensed motion information.

The wearable electromyogram sensor system 10 in accordance with the embodiment of the present invention includes the plurality of electrodes 110 installed on the surface of the band 100, and the electromyogram sensor 200 may be coupled to a desired position of the band 100. Thus, the wearable electromyogram sensor system 10 may easily acquire bio-signals of a body part to be measured.

Figure 5:
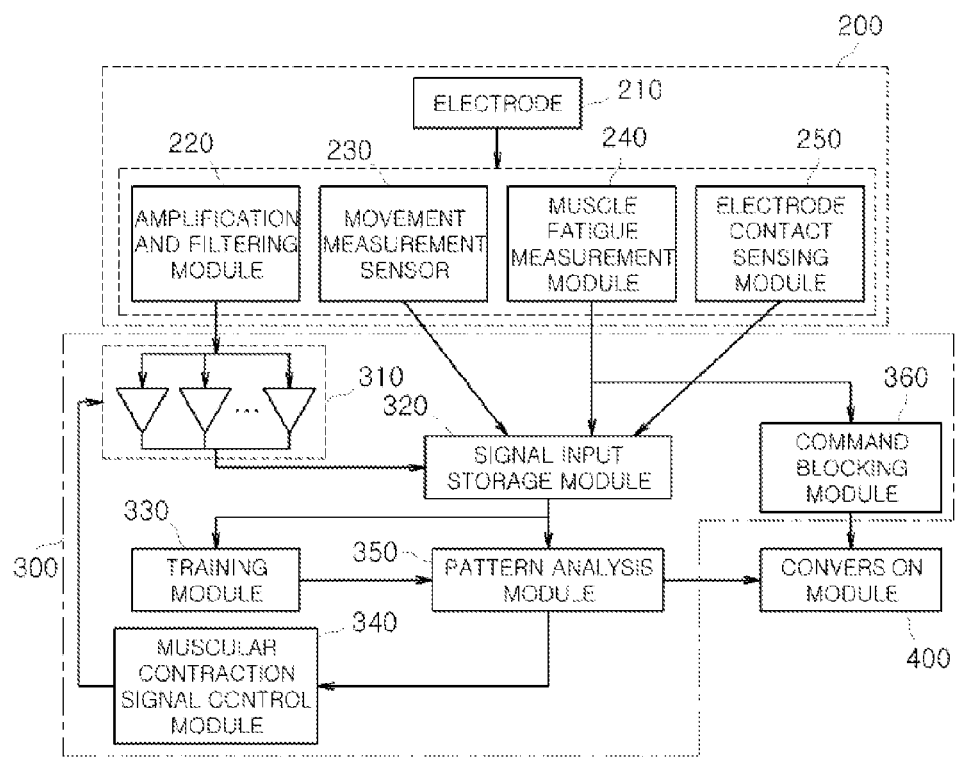
FIG. 5 is a block diagram illustrating the configuration of the wearable electromyogram sensor system in accordance with the embodiment of the present invention.

FIG. 5 is a block diagram illustrating the configuration of the wearable electromyogram sensor system in accordance with the embodiment of the present invention.

Referring to FIG. 5, the wearable electromyogram sensor system 10 in accordance with the embodiment of the present invention includes the band 100, the electromyogram sensor 200, a controller 300, and a conversion module 400.

The electromyogram sensor 200 includes the electrode 210 connected to the electrode 110 of the band 100 as described above. The electromyogram sensor 200 may further include an amplification and filtering module 220, a movement measurement sensor 230, a muscle fatigue measurement module 240, and an electrode contact sensing module 250.

The amplification and filtering module 220 serves to amplify and filter a bio-signal generated by contraction and relaxation of a user's muscle. As the amplification and filter module 220 amplifies and filters the bio-signal, unnecessary noise may be removed, and a measurement signal for post processing may be extracted.

The movement measurement sensor 230 serves to measure the movement and posture of a body part to be measured in a state where the electromyogram sensor 200 is coupled to the band 100. When the electromyogram sensor 200 acquires bio-signals based on a motion of the same body part of a user, the acquired bio-signals may be slightly changed depending on the movements and postures of the user. For example, a bio-signal sensed when the user clenches and opens his/her fist in a state where the user does not move his/her arm and a bio-signal sensed when the user clenches and opens his/her fist while shaking his/her arm may be sensed as different bio-signals due to the influence of gravity or the like, even though the user clenches and opens his/her fist during both of the motions. The movement measurement sensor 230 may measure the movement and posture of a part to be measured, and then reflect information on the measured movement and posture when the bio-signals are processed. For example, a gyrosensor, an inertial measurement unit (IMU) sensor, an accelerator or the like may be used as the movement measurement sensor 230.

The muscle fatigue measurement module 240 serves to mechanically or optically measure fatigue accumulated in a user's muscle. When the user repeats the same motion, an error may occur in bio-signals sensed by the electromyogram sensor 200 due to the fatigue accumulated in the muscle. The muscle fatigue measurement module 240 measures the fatigue of the muscle and determines whether a muscle motion is normal or not. Then, the muscle fatigue measure module 240 provides information required for predicting which motion the user is intended to execute. The kind of the muscle fatigue measurement module 240 is not limited. For example, an accelerator to measure vibrations of muscles or an infrared sensor to measure oxygen saturation may be used.

The electrode contact sensing module 250 serves to sense a contact state between the electrode 110 of the band 100 and the electrode 210 of the electromyogram sensor 200. In order to smoothly acquire bio-signals, the connection between the electrode 110 of the band 100 and the electrode 210 of the electromyogram sensor 200 must be reliably guaranteed. The electrode contact sensing module 250 senses the connection state between the electrodes, thereby preventing a false signal from being measured. The kind of the electrode contact sensing module 250 is not limited. For example, a temperature sensor, an infrared sensor, or an electrical ground signal may be used.

The controller 300 serves to analyze the pattern of bio-signals transmitted from the electromyogram sensor 200, sense or previously sense a change of the motion information to sense or predict a motion intended by the user, and transmit the sensed or predicted motion information to the conversion module 400.

Specifically, the controller 300 may include a muscular contraction signal processing module 310, a signal input storage module 320, a training module 330, a muscular contraction signal control module 340, a pattern analysis module 350, and a command blocking module 360.

The muscular contraction signal processing module 310 serves to individually or integrally amplify or attenuate muscular contraction signals transmitted from the amplification and filtering module 220 of the electromyogram sensor 200. The muscular contraction signal processing module 310 corrects the inaccuracy of signal processing, which may be caused by interference and noise introduction between adjacent muscular contraction signals, a distance between a body part to be measured and a muscle in which an electromyogram signal occurs, or a posture of a motion to be measured.

The signal input storage module 320 serves to receive and store measurement signals sensed by the electromyogram sensor 200 in real time. Specifically, the signal input storage module 320 may receive and store the measurement signals sensed by the amplification and filtering module 220, the movement measurement sensor 230, the muscle fatigue measurement module 240, and the electrode contact sensing module 250.

The training module 330 serves to previously receive information on movements, postures, and muscular contractions of a user, which occur before a predetermined motion of the user. The training module 330 may receive various pieces of information on movements, postures, and muscular contractions of users, which are slightly different from each other depending on the physical features of the respective users. When information on movements, postures, and muscular contractions of a specific user, sensed by the electromyogram sensor 200 is received by the training module 330, a motion intended by the user may predicted based on the received user information.

The muscular contraction signal control module 340 serves to control the amplification and attenuation for muscular signals, in order to optimize pattern analysis of the pattern analysis module 350. The muscular contraction signal control module 340 may include a process of optimizing pattern analysis based on the distribution of muscles used by a user and a process of dealing with a signal change depending on muscle fatigue. The signal processed by the muscular contraction signal control module 340 may be fed back to the muscular contraction signal processing module 310 and then reprocessed.

The pattern analysis module 350 serves to analyze the pattern of gesture, force, or energy distribution of the user based on the measurement signals of the electromyogram sensor 200, transmitted from the signal input storage module 320 in real time, and the information inputted from the training module 330. The pattern analysis module 350 may correct the measurement signals based on the information of the movement measurement sensor 230 and the training module 330.

For example, when the user lifts and lowers his/her arm, a case in which the pattern of measured muscle signals is changed due to the influence of gravity may be considered.

First, when a motion intended by the user can be distinguished through signals measured by the movement measurement sensor 230, the intended motion of the user is sensed or predicted based on the measured signals of the movement measurement sensor 230 and the information of the training module 330.

When the motion intended by the user cannot be distinguished through the measured signals of the movement measurement sensor 230, the signal patterns of the amplification and filtering module 220 and the movement measurement sensor 230 and the information of the training module 330 are compared and analyzed to sensor or predict the intended motion of the user.

When the amplification and filtering module 220 generates various types of signals for the same measured signals of the movement measurement sensor 230, the signals of the amplification and filtering module 220 and the information of the training module 330 may be compared and analyzed to predict the intended motion of the user. For example, when a user grabs an object by his/her hand, the movement measurement sensor 230 generates the same signals because motions of fingers do not occur. However, the amplification and filtering module 220 may generate different signals depending on how the user applies force to his/her fingers. In this case, the amplification and filtering module 220 processes muscular contraction signals generated from different muscles depending on how the user applies force to his/her fingers. Then, the processed signals may be compared to the information of the training module 330 so as to sense or predict the intended motion of the user.

The controller 300 may further include a command blocking module 360 to block a command using an electromyogram signal depending on the fatigue of a muscle. When the fatigue of a muscle based on a signal transmitted from the muscle fatigue measurement module 240 exceeds a predetermined critical value, the command block module 360 determines that the muscular contraction signal is not a normal muscular contraction signal, and blocks a command based on the user's muscular contraction signal from being transmitted to the conversion module 400.

The conversion module 400 serves to convert information into one or more of motion, energy, force, sound, image, tactility, and data based on the pattern analysis for user's motions. For example, when the user raises his/her thumb, the conversion module 400 may convert a signal measured for the user's muscle into a command for controlling a robot to raise its thumb, a command for outputting a sound through an audio device, and a command for displaying 'BEST' on a display device.

The conversion module 400 may be set to a data input device and connected to a data processing device such as a computer, thereby constructing a human-computer interface (HCI). Thus, the HCI may recognize a user's motion as data and input the recognized data to the data processing device such that the data processing device sensitively responds to the user's motion, instead of using a data input device such as a keyboard or mouse.

Figure 6A:
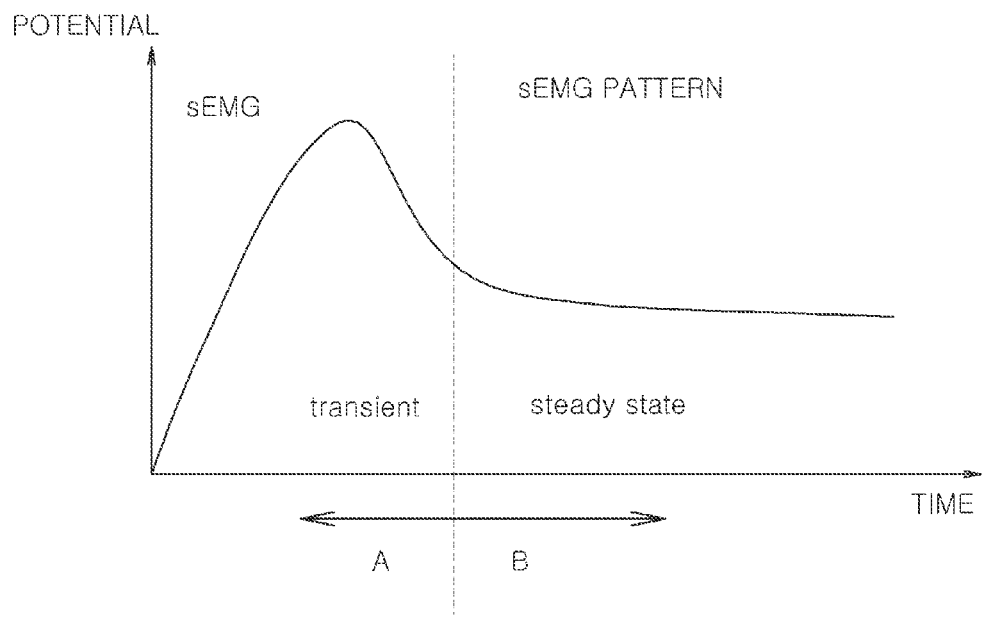
FIG. 6A is a diagram illustrating changes of a surface electromyogram (SEMG) signal before and after motion.
Figure 6B:
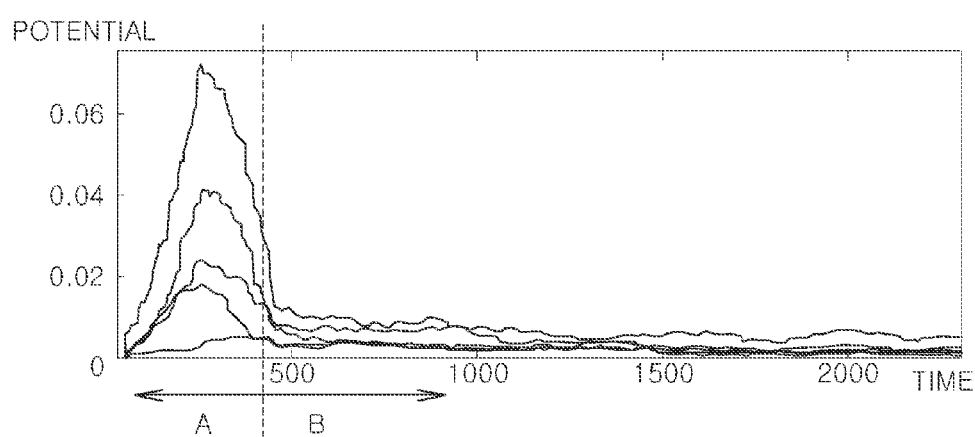
FIG. 6B is a diagram illustrating changes of a experimentally-measured SEMG signal before and after motion.

FIG. 6A is a diagram illustrating changes of an SEMG signal before and after motion, and FIG. 6B is a diagram illustrating changes of a substantially-measured SEMG signal before and after motion.

Referring to FIG. 6A, the SEMG signal before and after motion is changed as illustrated in the drawing.

When an SEMG signal before and after a unit motion is changed, a motor unit motion potential (MUAP) is changed according to the occurrence of the unit motion. Referring to FIG. 6A, the left side of a dotted line indicates the changes of the SEMG signal before the motion occurs, and the potential rapidly increases and decreases in a transient state (section A) before motion. The right side of the dotted line indicates the changes of the SEMG signal after the motion occurred, and the SEMG signal has a constant value in a steady state (section B) after motion.

That is, the SEMG signal before and after motion has different patterns, and the patterns may be analyzed to predict or recognize the motion. For example, the SEMG signal in the transient state (section A) may be analyzed to predict the motion, or the SEMG signal in the steady state (section B) may be analyzed to recognize the motion.

FIG. 6B is a diagram illustrating the changes of the substantially-measured SEMG signal before and after motion. The left side of a dotted line indicates a transient state (section A) before a motion occurs, and the right side of the dotted line indicates a steady state (section B) after the motion occurred.

Referring to FIG. 6B, the magnitude or form of the SEMG signal may be slightly changed depending on motions, magnitudes of force, directions of force, or energy distribution. Thus, the electromyogram sensor system according to the embodiment of the present invention may analyze the SEMG signal in the transient state (section A) to predict motion information of the wearer, or analyzes the SEMG signal in the steady state (section B) to recognize the motion information of the wearer.

In accordance with the embodiment of the present invention, although the wearer does not move, the bio-signal of the transient state (section A) may be analyzed to predict motion information such as motion, a magnitude of force, a direction of force, or energy distribution.

That is, in accordance with the embodiment of the present invention, the motion information not only may be sensed through a visual sensor or gyrosensor even after a motion of a terminal part such as a hand occurred, but also may be predicted through the analysis of bio-signals even though a motion of a terminal part does not occur.

The function of the conversion module 400 will be described in more detail with reference to FIGS. 7 to 9.

Figure 7:
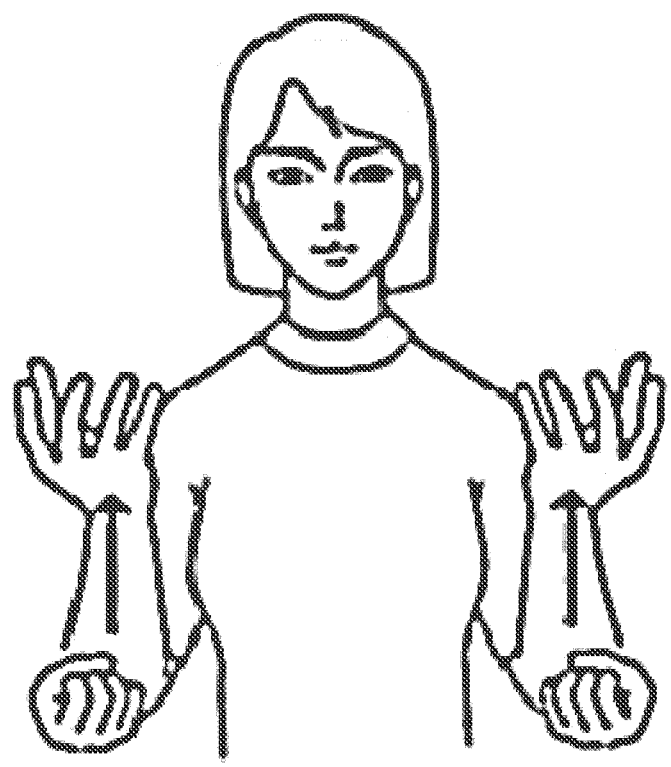
FIG. 7 is a diagram for explaining a function of the conversion module of FIG. 5.

FIG. 7 is a diagram for explaining a function of the conversion module of FIG. 5.

Referring to FIG. 7, the conversion module 400 may include a device to convert sign language into sound based on pattern analysis for gestures of a user wearing the electromyogram sensor 200. The electromyogram sensor 200 may sense a meaningful motion or gesture of the user, and the conversion module 400 may convert the sensed motion or gesture into sound, visual information, or command information such that the motion or gesture is displayed to the outside.

Figure 8:
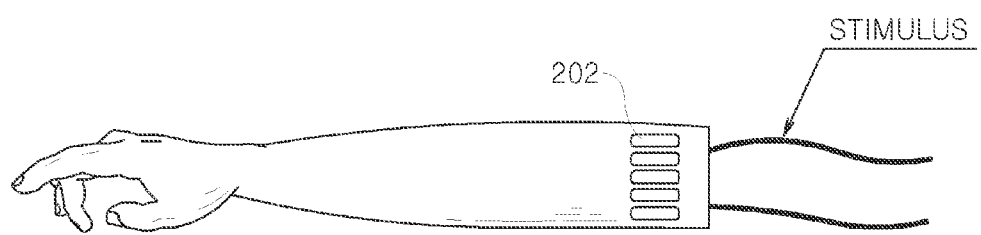
FIG. 8 is a diagram for explaining another function of the conversion module of FIG. 5.

FIG. 8 is a diagram for explaining another function of the conversion module of FIG. 5.

FIG. 8 illustrates that a surface electromyography (sEMG) sensor system 202 is attached on a user's damaged arm, and a stimulus is applied to a neuronal signal so as to check whether the neuronal signal is normally connected. When the sEMG sensor system 202 senses a temperature change or vibration of a muscle in response to the neuronal stimulus, the conversion module 400 converts the sensed temperature change or vibration into sound or visual information, and displays the information to the outside. Then, the user may check whether or not there is nerve damage, in real time.

Figure 9:
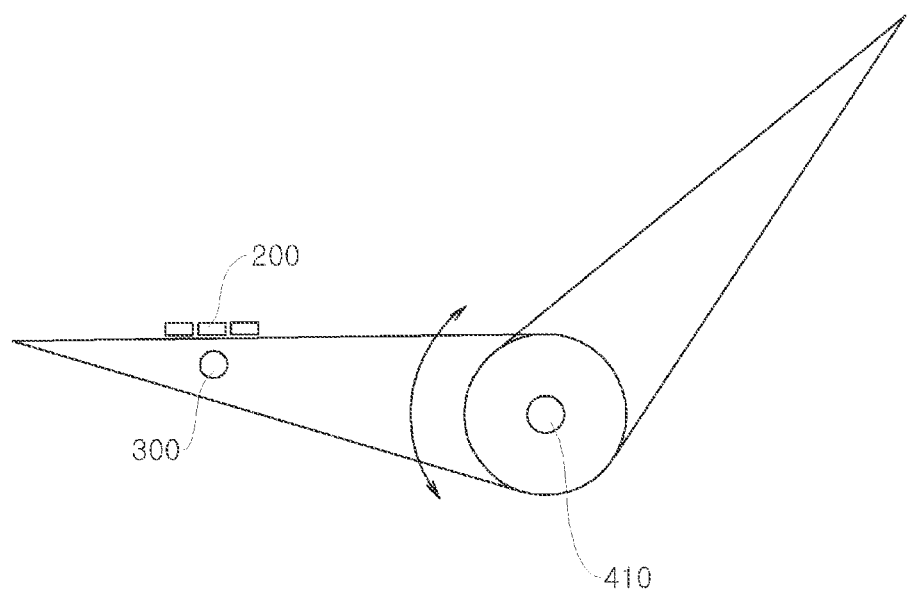
FIG. 9 is a diagram for explaining another function of the conversion module of FIG. 5.

FIG. 9 is a diagram for explaining another function of the conversion module of FIG. 5.

Referring to FIG. 9, the conversion module may include an actuator 410 to convert the motion information sensed by the electromyogram sensor 200 into the same motion as or a motion corresponding to the motion information.

The electromyogram sensor 200 senses a bio-signal inside the body, and the controller 300 predicts an intended motion of the user based on pattern analysis for the bio-signal. The motion information predicted by the controller 300 is transmitted to the conversion module 400, and the conversion module 400 converts the bio-signal of the body into a motion of the body through the actuator 410. The conversion module 400 may be usefully applied to a rehabilitation treatment of a patient whose body is partially damaged.

For example, the electromyogram sensor 200 may be attached to a patient whose leg muscles or nerves are partially damaged. Then, when a signal measured for muscles related to a motion of the leg is sensed, the conversion module 400 may drive the actuator 410 and provide power to assist a patient who has weak muscles and has difficulties in walking. Thus, a leg rehabilitation training of a patient whose leg is damaged may be executed.

Although not illustrated in the drawings, the conversion module may include a remote control device or an artificial arm which converts the motion information sensed by the electromyogram sensor into a motion corresponding to the motion information, while separated from the user. The orthosis may include as a prosthetic arm, hand, or leg which may be applied to an amputee.

That is, the remote control device or orthosis may convert the motion information sensed by the electromyogram sensor into the same motion as or a motion or energy corresponding to the motion information, while separated from the user. For example, a remote control device such as a robot or prosthetic hand may be applied to the electromyogram sensor system so as to be remote-controlled by a user.

For example, the electromyogram sensor system may predict or recognize a magnitude of force through a motion of a user who is grabbing or pushing an object, transmit the predicted or recognized magnitude to the remote control device. Then, the remote control device may convert the transmitted magnitude into force or energy equal to or proportional to the magnitude of force of the user such that the user executes a motion.

In accordance with the embodiments of the present invention, since the wearable electromyogram sensor system includes the elastic band having a plurality of electrodes formed through the surface thereof, a user may wear the band on various body parts having different thicknesses and sizes and then couple the electromyogram sensor to a desired position of the band. Thus, bio-signals of a body part to be measured may be easily acquired.

Furthermore, the wearable electromyogram sensor system may predict a motion before the motion is executed or recognize a motion after the motion was executed, based on bio-signals measured by the electromyogram sensor. Thus, the wearable electromyogram sensor system may assist various commands or motions intended by a user from the predicted or recognized motion.

Furthermore, the electromyogram signal of the wearable electromyogram sensor system according to the embodiment of the present invention may be affected by the movement and posture of a wearer. Thus, the movement measurement sensor for reflecting the movement and posture of the wearer may be coupled to more precisely and accurately recognize a motion.

Furthermore, the wearable electromyogram sensor system according to the embodiment of the present invention may include the muscle fatigue measurement module for correcting an error which may occur due to fatigue of the wearer, and may reflect the error correction to improve reliability.

While the present invention has been described with respect to the specific embodiments, it will be apparent to those skilled in the art that various changes and modifications may be made without departing from the spirit and scope of the invention as defined in the following claims.

What is claimed is:

1. A wearable electromyogram sensor apparatus, comprising:
    an elastic band comprising electrodes installed through a surface of the elastic band:
    an electromyogram sensor comprising an electrode connected to another electrode of the band so as to receive a bio-signal related to a contraction of a muscle;

a controller in communication with the electrode and configured to determine a change of motion information of the bio-signal prior to a motion resulting from the contraction of the muscle by sensing a motion potential increase and decrease during a transient state of the bio-signal; and a fixing device configured to fix the electromyogram sensor to the band, wherein the electrode of the electromyogram sensor is connected to the another electrode at an arbitrary position on the band, wherein the bio-signal comprises the transient state and a steady state, and the transient state occurs immediately prior to the motion and the steady state occurs during the motion, wherein a motion potential increases and thereafter decreases during the transient state, and the controller is further configured to detect the motion potential increase and decrease during the transient state and prior to the motion, and wherein the motion information comprises direction of force, magnitude of force, energy distribution through the bio-signal related to the motion, muscle fatigue, posture, and a comparison to stored motion data of resultant motions determined to be similar to the motion.

2. The wearable electromyogram sensor apparatus of claim 1, wherein
the fixing device comprises a fastener comprising any one of a magnet, hook and loop, and a detachable tape, and
the fastener is attached to the band and the electromyogram sensor.

3. The wearable electromyogram sensor apparatus of claim 1, wherein
the electromyogram sensor comprises an amplifier and filter configured to amplify and filter the bio-signal,
a movement measurement sensor configured to measure a movement and a posture of a part to be measured, in response to the electromyogram sensor being coupled to the band,
a muscle fatigue measurement sensor configured to mechanically or optically measure fatigue accumulated in the muscle, and
an electrode contact sensor configured to sense a contact state between the electrode of the band and the electrode of the electromyogram sensor.

4. The wearable electromyogram sensor apparatus of claim 1, wherein the electromyogram sensor comprises
an amplifier and filter configured to amplify and filter the bio signals;
a movement measurement sensor configured to measure a movement and posture of a part to be measured, and
a muscle fatigue measurement sensor configured to mechanically or optically measure fatigue accumulated in the muscle.

5. The wearable electromyogram sensor system of claim 1, further comprising a controller configured to analyze a pattern of the bio-signal and to sense the change of the motion information, and a conversion device configured to convert the change of the motion information into any one or any combination of any two or more of motion, energy, force, sound, image, tactility, and data based on the analysis of the pattern.

6. The wearable electromyogram sensor apparatus of claim 5, wherein the controller comprises a muscular contraction signal processing module configured to individually or integrally amplify or attenuate the bio-signals transmitted from the electromyogram sensor, a training module configured to receive information on a user's movement, posture, and muscle contraction which occur before the motion, which is of the user, a pattern analysis module configured to analyze a pattern of the motion based on the bio-signals measured by the electromyogram sensor and information inputted from the training module, and a signal input storage module configured to receive and store the bio-signals measured by the electromyogram sensor in real time.

7. The wearable electromyogram sensor apparatus of claim 6, wherein the controller further comprises a muscular contraction signal control module configured to control amplification and attenuation for the analyzing of the pattern of the motion.

8. The wearable electromyogram sensor apparatus of claim 5, wherein the controller further comprises a command block module configured to determine that a muscular contraction signal is abnormal, in response to muscle fatigue exceeding a critical value, and to block a command based on the user's bio-signals from being transmitted to the conversion device.

9. The wearable electromyogram sensor apparatus of claim 5, wherein the conversion device comprises a device configured to convert sign language into sound based on pattern analysis of the motion.

10. The wearable electromyogram sensor apparatus of claim 5, wherein the conversion device comprises an actuator configured to convert the motion information sensed by the electromyogram sensor into a same motion as the motion information or a motion corresponding to the motion information.

11. The wearable electromyogram sensor apparatus of claim 5, wherein the conversion device comprises a remote control device or an orthosis configured to convert the motion information sensed by the electromyogram sensor into a same motion as the motion information or a motion corresponding to the motion information, while being separated from the user.

12. The wearable electromyogram sensor apparatus of claim 1, wherein the electromyogram sensor comprises a display configured to display any one or any combination of any two or more of a sound signal, an image signal, and a tactile signal corresponding to the sensed motion information.

13. The wearable electromyogram sensor apparatus of claim 1, wherein the electromyogram sensor is configured to sense the change of motion information while the motion information is being changed.

14. The wearable electromyogram sensor apparatus of claim 1, wherein the electromyogram sensor is configured to sense the change of motion information while the motion information is being changed.

15. The wearable electromyogram sensor apparatus of claim 1, wherein the motion information consists of the direction of force, the magnitude of force, the energy distribution through the bio-signal related to the motion, the posture, the muscle fatigue, and the comparison to the stored motion data of the similar resultant motions.

16. The wearable electromyogram apparatus of claim 7, wherein
the electromyogram sensor further comprises a movement measurement sensor, and the pattern analysis module is further configured to predict an intended motion of the user based on measured signals of the movement measurement sensor and the information of the training module, in response to determining that a motion intended by the user can be distinguished through signals measured by the movement measurement sensor.

17. The wearable electromyogram apparatus of claim 16, wherein the electromyogram sensor further comprises an amplification and filtering module, and the pattern analysis module is further configured to predict the intended motion of the user by comparing and analyzing the signal patterns of the amplification and filtering module, the movement measurement sensor, and information of the training module, in response to determining that the motion intended by the user cannot be distinguished through the measured signals of the movement measurement sensor.

18. The wearable electromyogram apparatus of claim 17, wherein the pattern analysis module is further configured to predict the intended motion of the user by comparing and analyzing signals of the amplification and filtering module and the information of the training module, in response to determining that the amplification and filtering module generates multiple types of signals for the measured signals of the movement measurement sensor.

19. The wearable electromyogram apparatus of claim 1, wherein during the transient state, the muscle does not cause movement of a body part and the bio-signal peaks, and during the steady state, the muscle causes movement of a body part and the bio-signal decays.

* * * * *